US00RE46928E

(19) United States
(12) Reissued Patent
Hulse et al.

(10) Patent Number: US RE46,928 E
(45) Date of Reissued Patent: Jul. 3, 2018

(54) AZEOTROPE-LIKE COMPOSITIONS OF PENTAFLUOROPROPENE AND WATER

(71) Applicant: THE CHEMOURS COMPANY FC, LLC, Wilmington, DE (US)

(72) Inventors: Ryan Hulse, Getzville, NY (US); Haluk Kopkalli, Staten Island, NY (US); Hang T. Pham, Amherst, NY (US)

(73) Assignee: THE CHEMOURS COMPANY FC, LLC, Wilmington, DE (US)

(21) Appl. No.: 15/429,745

(22) Filed: Feb. 10, 2017

Related U.S. Patent Documents

Reissue of:
(64) Patent No.: 8,951,431
Issued: Feb. 10, 2015
Appl. No.: 13/083,230
Filed: Apr. 8, 2011

U.S. Applications:
(60) Provisional application No. 61/331,971, filed on May 6, 2010.

(51) Int. Cl.

| | |
|---|---|
| ***C09K 5/04*** | (2006.01) |
| ***C07C 17/386*** | (2006.01) |
| ***C07C 17/38*** | (2006.01) |
| ***C07C 17/383*** | (2006.01) |
| ***C07C 17/389*** | (2006.01) |

(52) U.S. Cl.
CPC ..... *C07C 17/386* (2013.01); *C07C 17/38* (2013.01); *C07C 17/383* (2013.01); *C07C 17/389* (2013.01)

(58) Field of Classification Search
CPC ..... C07C 17/386
USPC ..... 252/67
See application file for complete search history.

(56) References Cited

U.S. PATENT DOCUMENTS

| | | | | |
|---|---|---|---|---|
| 7,794,618 | B2 | 9/2010 | Pham et al. | |
| 8,288,597 | B2 * | 10/2012 | Rao et al. | 570/156 |
| 8,410,325 | B2 * | 4/2013 | Sharratt et al. | 570/160 |
| 2006/0106263 | A1 * | 5/2006 | Miller et al. | 570/155 |
| 2007/0099811 | A1 * | 5/2007 | Miller et al. | 510/408 |
| 2007/0100173 | A1 * | 5/2007 | Miller et al. | 570/178 |
| 2008/0011678 | A1 | 1/2008 | Knapp et al. | |
| 2008/0051611 | A1 * | 2/2008 | Wang et al. | 570/166 |
| 2008/0051612 | A1 | 2/2008 | Knapp et al. | |
| 2009/0012336 | A1 | 1/2009 | Nappa et al. | |
| 2009/0151365 | A1 | 6/2009 | Pham et al. | |
| 2009/0234165 | A1 | 9/2009 | Chiu et al. | C07C 17/23 570/136 |
| 2010/0048961 | A1 | 2/2010 | Merkel et al. | |
| 2010/0119460 | A1 * | 5/2010 | Pham et al. | 424/47 |
| 2010/0162738 | A1 * | 7/2010 | Low et al. | B01D 53/261 62/101 |
| 2011/0160500 | A1 * | 6/2011 | Takahashi | 570/175 |
| 2011/0172472 | A1 * | 7/2011 | Sakyu et al. | 570/160 |
| 2011/0190554 | A1 * | 8/2011 | Pigamo et al. | 570/155 |
| 2011/0275723 | A1 * | 11/2011 | Hulse et al. | 514/772 |
| 2011/0275724 | A1 * | 11/2011 | Hulse et al. | 514/772 |
| 2012/0056122 | A1 * | 3/2012 | Hulse et al. | 252/67 |
| 2012/0065435 | A1 * | 3/2012 | Nishiguchi et al. | 570/164 |
| 2012/0128964 | A1 * | 5/2012 | Hulse et al. | 428/305.5 |
| 2012/0283339 | A1 * | 11/2012 | Bowman et al. | 516/12 |
| 2013/0060069 | A1 * | 3/2013 | Elsheikh et al. | 570/156 |

FOREIGN PATENT DOCUMENTS

| | | | | |
|---|---|---|---|---|
| FR | 2935702 | A1 * | 3/2010 | C07C 17/25 |
| GB | 2439209 | A * | 12/2007 | |
| GB | 2439209 | B * | 11/2008 | B01D 53/261 |
| WO | 02/100506 | A1 | 12/2001 | |
| WO | 2006/094303 | A2 | 9/2006 | |
| WO | 2007/144632 | A1 | 12/2007 | |
| WO | 2008/024508 | A1 | 2/2008 | |
| WO | 2008/030444 | A2 | 3/2008 | |
| WO | 2008/033568 | A2 | 3/2008 | |
| WO | 2011/139945 | A2 | 11/2011 | |

OTHER PUBLICATIONS

Kim, et al., "A Study to Determine the Existence of an Azeotropic R-22 "Drop-In" Substitute," prepared by U.S. Department of Commerce for Electric Power Research Institute, Mar. 1996, pp. 1-45, U.S.

Morrison, et al., "Azeotropy in Refrigerant Mixture," International Journal of Refrigeration, 1993, pp. 129-138, vol. 16, No. 2. U.S.

Morrison, Graham et al., Azeotropy in refrigerant mixtures, International Journal of Refrigeration, 1993, pp. 129-138, vol. 16 No. 2.

Raabe, Gariele, Molecular Modeling of Fluoropropene Refrigerants, The Journal of Physical Chemistry B, 2012, pp. 5744-5751, vol. 116.

* cited by examiner

*Primary Examiner* — Timothy J. Kugel

(57) ABSTRACT

Provided are azeotropic and azeotrope-like compositions of 1,2,3,3,3-pentafluoropropene (HFO-1225ye) and water. Such azeotropic and azeotrope-like compositions are useful in isolating 1,2,3,3,3-pentafluoropropene from impurities during production. Azeotropes of the instant invention are similarly useful in final compositions or manufacturing final compositions, such as blowing agent, propellants, refrigerants, diluents for gaseous sterilization and the like.

108 Claims, No Drawings

AZEOTROPE-LIKE COMPOSITIONS OF PENTAFLUOROPROPENE AND WATER

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

This application is related to and claims the priority benefit of U.S. provisional application Ser. No. 61/331,971, filed May 6, 2010, the contents of which are incorporated herein by reference.

FIELD OF THE INVENTION

The present invention pertains to azeotropic and azeotrope-like compositions of 1,2,3,3,3-pentafluoropropene (HFO-1225ye) and water.

BACKGROUND OF THE INVENTION

Traditionally, chlorofluorocarbons (CFCs) like trichlorofluoromethane and dichlorodifluoromethane have been used as refrigerants, blowing agents and diluents for gaseous sterilization. In recent years, there has been universal concern that completely halogenated chlorofluorocarbons might be detrimental to the Earth's ozone layer. Therefore, stratospherically safer alternatives to these materials are desirable.

There is presently a worldwide effort to use fluorine-substituted hydrocarbons which contain fewer or no chlorine substituents. The production of HFCs, i.e. compounds containing only carbon, hydrogen and fluorine, has been the subject of interest to provide environmentally desirable products that could provide a substitute to CFCs. Such compounds are known in the art to be produced by reacting hydrogen fluoride with various hydrochlorocarbon compounds. While HFCs are considered to be much more environmentally advantageous than hydrochlorofluorocarbons (HCFCs) or chlorofluorocarbons (CFCs) because they are not non-ozone depleting, recent data indicates that they may also contribute to greenhouse global warming. Accordingly, alternatives to HFCs, HCFCs, and CFCs are also being explored.

Hydrofluoroolefins ("HFOs") have been proposed as possible replacements. Two such HFOs are 1,2,3,3,3-pentafluoropropene (HFO-1225ye) and 2,3,3,3-tetrafluoropropene (HFO-1234yf). As disclosed in US 20090234165, the contents of which are incorporated herein by reference, HFO-1225ye is known to be produced as an intermediate in the production of HFO-1234yf. Each of these HFOs have been well characterized as effective refrigerant, heat transfer medium, propellant, foaming agent, blowing agent, gaseous dielectric, sterilant carrier, polymerization medium, particulate removal fluid, carrier fluid, buffing abrasive agent, displacement drying agent and power cycle working fluid.

It is, nevertheless, generally known that HFOs are best used as a single component fluid or azeotropic mixture, neither of which fractionate upon boiling and evaporation. The identification of such compositions is difficult due, at least in part, to the relative unpredictability of azeotrope formation. Therefore, industry is continually seeking new HFO-based mixtures that are acceptable and environmentally safer substitutes for CFCs, HCFCs, and HFCs. This invention satisfies these needs among others.

SUMMARY OF THE INVENTION

The invention provides an azeotropic or azeotrope-like composition of 1,2,3,3,3-pentafluoropropene (HFO-1225ye) and water. The compositions of the instant invention provide environmentally desirable replacements for currently used CFCs, HFCs and HCFCs, since HFO-1225ye and water have little to no ozone depletion potential. Additionally, a composition containing such an azeotrope exhibits characteristics that make it better than CFCs, HFCs, and HCFCs substitutes, as well as either HFO-1225ye or water alone.

The invention further provides a composition and method of forming an azeotropic or azeotrope-like composition which comprises a blend of from about 0.1 to about 50 weight percent water and about 50 to 99.9 weight percent HFO-1225ye. In further embodiments, the azeotropic or azeotrope-like composition comprises a blend of from about 0.1 to about 25 weight percent water and about 75 to 99.9 weight percent HFO-1225ye, and in even further embodiments it comprises a blend of from about 0.25 to about 11 weight percent water and about 89 to 99.75 weight percent HFO-1225ye. The resulting azeotrope has a boiling point of about −20° C.±0.5° C. at a pressure of about 14.3 psia±2 psia. In further embodiments, the azeotrope has a boiling point of about −20° C. at a pressure of about 14.3 psia, and in even further embodiments, the azeotrope has a boiling point of about −20.3° C. at a pressure of about 14.39 psia.

The instant invention also relates to a method for removing 1,2,3,3,3-pentafluoropropene from a mixture containing 1,2,3,3,3-pentafluoropropene and at least one impurity by adding water to the mixture in an effective amount to form an azeotropic or azeotrope-like composition in accordance with the foregoing. This azeotrope is then separated from impurities using standard methods known in the art, such as but not limited to, distillation. Impurities may include a halocarbon or hydrogen fluoride, which may or may not be miscible with 1,2,3,3,3-pentafluoropropene. Examples of halocarbons include, but are not limited to, 1,1,1,2,3,3-hexafluoropropane (HFC-236ea); 1,1,1,2,3-pentafluoropropane (HFC-245eb); hexafluoropropylene (HFP); 1,1,1,2-tetrafluoropropene (HFO-1234yf); and combinations thereof. In further embodiments, the impurities may or may not also form an azeotropic mixture 1,2,3,3,3-pentafluoropropene, water or a mixture of 1,2,3,3,3-pentafluoropropene and water.

The instant invention also relates to a method for isolating 1,2,3,3,3-pentafluoropropene from an azeotropic mixture of 1,2,3,3,3-pentafluoropropene and water, by separating 1,2,3,3,3-pentafluoropropene from the water. Separation methods may include any one or combination of methods known in the art or otherwise discussed herein. For example, 1,2,3,3,3-pentafluoropropene may be separated using a liquid-liquid phase separation. In alternative embodiments, 1,2,3,3,3-pentafluoropropene may be separated using distillation and/or one or more drying media (e.g. a molecular sieve, silica alumina, or the like). In further embodiments, separation methods may include a combination of liquid-liquid phase separation and a second method selected from distillation and/or one or more drying media.

Additional embodiments and advantages of the instant invention will be apparent to one of ordinary skill in the art, based on the disclosure provided herein.

DETAILED DESCRIPTION OF THE INVENTION

In one aspect of the instant invention, an azeotropic or azeotrope-like composition is provided of 1,2,3,3,3-pentafluoropropene (HFO-1225ye) and water. This composition provides environmentally desirable replacements for currently used CFCs, HFCs, and HCFCs, since HFO-1225ye and water have little to no ozone depletion potential. Additionally, a composition containing such an azeotrope exhibits characteristics that make it better than CFC, HFC, and HCFC substitutes, as well as HFO-1225ye or water alone. In another aspect of the instant invention, the azeotrope or azeotrope-like composition of HFO-1225ye and water is used to isolate a purified form of HFO-1225ye. As used in this invention, "HFO-1225ye" refers to either the "E" or the "Z" isomers individually or a mixture thereof.

For purposes of this invention, azeotrope or azeotrope-like mixtures of HFO-1225ye and water, include those compositions or mixtures that behave like azeotropes. The thermodynamic state of a fluid is defined by its pressure, temperature, liquid composition and vapor composition. For a true azeotropic composition, the liquid composition and vapor phase are essentially equal at a given temperature and pressure range. In practical terms this means that the components cannot be separated during a phase change. For the purpose of this invention, an azeotrope is a liquid mixture that exhibits a maximum or minimum boiling point relative to the boiling points of surrounding mixture compositions. An azeotrope or an azeotrope-like composition is an admixture of two or more different components which, when in liquid form under given pressure, will boil at a substantially constant temperature, which temperature may be higher or lower than the boiling temperatures of the components and which will provide a vapor composition essentially identical to the liquid composition undergoing boiling. For the purpose of this invention, azeotropic compositions are defined to include azeotrope-like compositions which means a composition that behaves like an azeotrope, i.e., has constant-boiling characteristics or a tendency not to fractionate upon boiling or evaporation. Thus, the composition of the vapor formed during boiling or evaporation is the same as or substantially the same as the original liquid composition. Hence, during boiling or evaporation, the liquid composition, if it changes at all, changes only to a minimal or negligible extent. This is in contrast with non-azeotrope-like compositions in which during boiling or evaporation, the liquid composition changes to a substantial degree. Accordingly, the essential features of an azeotrope or an azeotrope-like composition are that at a given pressure, the boiling point of the liquid composition is fixed and that the composition of the vapor above the boiling composition is essentially that of the boiling liquid composition, i.e., essentially no fractionation of the components of the liquid composition takes place. Both the boiling point and the weight percentages of each component of the azeotropic composition may change when the azeotrope or azeotrope-like liquid composition is subjected to boiling at different pressures. Thus, an azeotrope or an azeotrope-like composition may be defined in terms of the relationship that exists between its components or in terms of the compositional ranges of the components or in terms of exact weight percentages of each component of the composition characterized by a fixed boiling point at a specified pressure.

Accordingly, the invention provides azeotrope-like compositions having effective amounts of HFO-1225ye and water. As used herein, "effective amounts" means an amount of each component that, on combination with the other component, results in the formation of an azeotrope-like composition. In certain embodiments, the azeotropic or azeotrope-like composition comprises a blend of from about 0.1 to about 50 weight percent water and about 50 to 99.9 weight percent HFO-1225ye. In further embodiments, the azeotropic or azeotrope-like composition comprises a blend of from about 0.1 to about 25 weight percent water and about 75 to 99.9 weight percent HFO-1225ye, and in even further embodiments azeotropic or azeotrope-like composition comprises a blend of from about 0.25 to about 11 weight percent water and about 89 to 99.75 weight percent HFO-1225ye. The azeotropic mixture of the present invention has a boiling point of about −20° C.±0.5° C. at a pressure of about 14.3±2 psia. In further embodiments, azeotropic mixture of the present invention has a boiling point of about −20° C. at a pressure of about 14.3. In an even further embodiment, the azeotrope has a boiling point of from about −20.3° C. at a pressure of from about 14.39 psia.

In one embodiment, the methods of the instant invention include the steps for generating the HFO-1225ye and HFO-1225ye/water azeotrope and for isolating the azeotrope from impurities. The instant methods also include steps for purifying HFO-1225ye from the azeotropic mixture, which are discussed in greater detail below. HFO-1225ye may be produced using one or more methods that are known in the art. In one non-limiting example, 1,2,3,3,3-pentafluoropropene (HFO-1225ye) is produced as an intermediate in the production of 2,3,3,3-tetrafluoropropene (HFO-1234yf) which is well known in the art as described in US Application No. 20090234165, the specifications of which are incorporated herein by reference. More specifically, HFO-1225ye may be produced by the initial hydrogenation of a hexafluoropropylene (HFP) to produce 1,1,1,2,3,3-hexafluoropropane (HFC-236ea). This is then used as a reactant in a dehydrohalogenation reaction to produce HFO-1225ye.

The first step in removing HFO-1225ye from this mixture, or any other mixture containing HFO-1225ye and an impurity, is by adding water in an effective amount, as defined herein, to form an azeotropic composition of the HFO-1225ye and water. Thereafter, the azeotropic composition is separated from the impurity using standard separation techniques, such as, but not limited to, distillation, scrubbing, or other art recognized separating means. In one embodiment, the impurity itself does not form an azeotropic mixture with HFO-1225ye, water or a mixture of HFO-1225ye and water. In another embodiment, the impurity does form an azeotropic mixture with HFO-1225ye, water or a mixture of HFO-1225ye and water. Typical impurities of HFO-1225ye include, but are not limited to, other halocarbons which may be miscible with HFO-1225ye such as, but not limited to, 1,1,1,2,3,3-hexafluoropropane (HFC-236ea); 1,1,1,2,3-pentafluoropropane (HFC-245eb); hexafluoropropylene (HFP); 1,1,1,2-tetrafluoropropene (HFO-1234yf); and combinations thereof. In further embodiments, the impurity is hydrogen fluoride.

This purified azeotrope meets the need in the art for HFO mixtures that have no ozone depletion potential and are negligible contributors to greenhouse global warming and are nonflammable. Such a mixture may be utilized in a wide range of uses such as, but not limited, refrigerants, blowing agents, propellants and diluents for gaseous sterilization. The azeotrope may be provided in combination with other useful additives or ingredients for such purposes.

Post-purification, it also may be desirable to separate component parts of the HFO-1225ye and water azeotrope to a purified form HFO-1225ye. Separation methods may include any method generally known in the art. In one embodiment, for example, the excess water can be removed from the HFO-1225ye by liquid-liquid phase separation. The remaining water can then be removed from the HFO-1225ye by distillation and/or one or more drying media (e.g. molecular sieves silica alumina, and the like). Purified HFO-1225ye may be used as an end product (i.e. as a refrigerant, blowing agent, propellant, diluents for gaseous sterilization, or the like), or it may be further processed for the production of alternative HFOs or similar compounds.

The following non-limiting examples serve to illustrate the invention.

EXAMPLES

Example 1

A glass vacuum insulated vessel fitted with a dry ice cooled condenser is initially charged with HFO-(Z)-1225ye. Water is then added incrementally and the temperature of the mixture is recorded. The temperature of the mixture reaches a minimum values and then flattens indicating the formation of a heterogeneous azeotrope. The ambient pressure during the measurements was 14.3 psia. The measured temperatures are shown in Table 1.

TABLE 1

Ebulliometer measurements of HFO-(Z)-1225ye and water at 14.39 psi

| water, wt % | Temp, ° C. |
|---|---|
| 0.00 | −20.19 |
| 0.25 | −20.31 |
| 0.75 | −20.32 |
| 1.74 | −20.31 |
| 3.65 | −20.31 |
| 7.26 | −20.31 |
| 10.61 | −20.31 |
| 13.73 | −20.32 |
| 16.64 | −20.32 |

We claim:

1. An azeotropic or azeotrope-like composition consisting essentially of 1,2,3,3,3-pentafluoropropene (HFO-1225ye) and water wherein water is provided in an amount from about 0.25 to about 11 weight percent and 1,2,3,3,3-pentafluoropropene is provided in an amount from about 89 to about 99.75 weight percent.

2. The composition of claim 1, consisting of water and 1,2,3,3,3-pentafluoropropene.

3. The composition of claim 1, having a boiling point of about −20° C.±0.5° C. at a pressure of about 14.3 psia±2 psia.

4. The composition of claim 1, having a boiling point of about −20° C. at a pressure of about 14.3 psia.

5. The composition of claim 1, having a boiling point of about −20.3° C. at a pressure of about 14.39 psia.

6. A method of forming an azeotropic or azeotrope-like composition comprising forming a blend consisting essentially of effective amounts of water and 1,2,3,3,3-pentafluoropropene, wherein water is provided in an amount from about 0.25 to about 11 weight percent and 1,2,3,3,3-pentafluoropropene is provided in an amount from about 89 to about 99.75 weight percent.

7. [The method of claim 6, wherein water is provided in an amount from about 0.25 to about 11 weight percent and 1,2,3,3,3-pentafluoropropene is provided in an amount from about 89 to about 99.75 weight percent.] The method of claim [9] *6*, wherein the *azeotropic or azeotrope-like* composition consists of water and 1,2,3,3,3-pentafluoropropene.

8. The method of claim 6, [having] *wherein the azeotropic or azeotrope-like composition has* a boiling point of about −20° C.±0.5° C. at a pressure of about 14.3 psia±2 psia.

9. The method of claim 6, [having] *wherein the azeotropic or azeotrope-like composition has* a boiling point of about −20° C. at a pressure of about 14.3 psia.

10. The method of claim 6, [having] *wherein the azeotropic or azeotrope-like composition has* a boiling point of about −20.3° C. at a pressure of about 14.39 psia.

11. A method for removing 1,2,3,3,3-pentafluoropropene from a mixture containing 1,2,3,3,3-pentafluoropropene and at least one impurity, comprising adding water to the mixture in an effective amount to form an azeotropic or azeotrope-like composition of the 1,2,3,3,3-pentafluoropropene and the water, and separating the azeotropic composition from the impurity, wherein water is provided in an amount from about 0.25 to about 11 weight percent and 1,2,3,3,3-pentafluoropropene is provided in an amount from about 89 to about 99.75 weight percent.

12. The method of claim 11, wherein the impurity does not form an azeotropic mixture with 1,2,3,3,3-pentafluoropropene, water or a mixture of 1,2,3,3,3-pentafluoropropene and water.

13. The method of claim 11, wherein the impurity does form an azeotropic mixture with 1,2,3,3,3-pentafluoropropene, water or a mixture of 1,2,3,3,3-pentafluoropropene and water.

14. The method of claim 11, wherein the impurity comprises a halocarbon.

15. The method of claim 11, wherein the impurity is miscible with 1,2,3,3,3-pentafluoropropene.

16. The method of claim 11, wherein the impurity is selected from the group consisting of hydrogen fluoride; 1,1,1,2,3,3-hexafluoropropane (HFC-236ea); 1,1,1,2,3-pentafluoropropane (HFC-245eb); hexafluoropropylene (HFP); 1,1,1,2-tetrafluoropropene (HFO-1234yf); and combinations thereof.

17. The method of claim 11, wherein the step of separating the azeotropic composition from the impurity is conducted by distillation.

18. The method of claim 11, wherein the azeotropic composition consists essentially of from about 0.1 to about 50 weight percent water and from about 50 to about 99.9 weight percent 1,2,3,3,3-pentafluoropropene.

19. A method for isolating 1,2,3,3,3-pentafluoropropene from an azeotropic mixture containing 1,2,3,3,3-pentafluoropropene and water, comprising separating 1,2,3,3,3-pentafluoropropene from the water, wherein water is provided in an amount from about 0.25 to about 11 weight percent and 1,2,3,3,3-pentafluoropropene is provided in an amount from about 89 to about 99.75 weight percent.

20. The method of claim 19, wherein 1,2,3,3,3-pentafluoropropene is separated from water using a liquid-liquid phase separation.

21. The method of claim 19, wherein 1,2,3,3,3-pentafluoropropene is separated from water using distillation.

22. The method of claim 19, wherein 1,2,3,3,3-pentafluoropropene is separated from water using at least one drying media.

23. The method of claim [19] *22*, wherein the drying media is selected from the group consisting of a molecular sieve, silica alumina, and combinations thereof.

24. The method of claim 19, wherein water is removed first by liquid-liquid phase separation, then by a second method selected from the group consisting of distillation, one or more drying media, and combinations thereof.

*25. The method of claim 6, further comprising:*

*producing 2,3,3,3-tetrafluoro-1-propene from the 1,2,3,3,3-pentafluoropropene.*

*26. The method of claim 11, further comprising:*

*producing 2,3,3,3-tetrafluoro-1-propene from the 1,2,3,3,3-pentafluoropropene.*

*27. The method of claim 11, wherein the mixture consists of water, 1,2,3,3,3-pentafluoropropene, and the impurity.*

*28. The method of claim 11, wherein the azeotropic or azeotrope-like composition has a boiling point of about −20° C.±0.5° C. at a pressure of about 14.3 psia±2 psia.*

*29. The method of claim 11, wherein the azeotropic or azeotrope-like composition has a boiling point of about −20° C. at a pressure of about 14.3 psia.*

*30. The method of claim 11, wherein the azeotropic or azeotrope-like composition has a boiling point of about −20.3° C. at a pressure of about 14.39 psia.*

*31. The method of claim 11,*

*wherein the impurity comprises hydrogen fluoride.*

*32. The method of claim 11,*

*wherein the impurity comprises 1,1,1,2,3,3-hexafluoropropane (HFC-236ea).*

*33. The method of claim 11,*

*wherein the impurity comprises 1,1,1,2,3-pentafluoropropane (HFC-245eb).*

*34. The method of claim 11,*

*wherein the impurity comprises hexafluoropropylene (HFP).*

*35. The method of claim 11,*

*wherein the impurity comprises 1,1,1,2-tetrafluoropropene (HFO-1234yf).*

*36. The method of claim 19, further comprising:*

*producing 2,3,3,3-tetrafluoro-1-propene from the 1,2,3,3,3-pentafluoropropene.*

*37. The method of claim 19, wherein the azeotropic mixture consists of water and 1,2,3,3,3-pentafluoropropene.*

*38. The method of claim 19, wherein the azeotropic mixture has a boiling point of about −20° C.±0.5° C. at a pressure of about 14.3 psia±2 psia.*

*39. The method of claim 19, wherein the azeotropic mixture has a boiling point of about −20° C. at a pressure of about 14.3 psia.*

*40. The method of claim 19, wherein the azeotropic mixture has a boiling point of about −20.3° C. at a pressure of about 14.39 psia.*

*41. A method, comprising:*

*forming a blend consisting essentially of effective amounts of water and 1,2,3,3,3-pentafluoropropene;*

*wherein water is provided in an amount from about 0.25 to about 11 weight percent and 1,2,3,3,3-pentafluoropropene is provided in an amount from about 89 to about 99.75 weight percent; and*

*producing 2,3,3,3-tetrafluoro-1-propene from the 1,2,3,3,3-pentafluoropropene.*

*42. The method of claim 41, wherein the blend consists of water and 1,2,3,3,3-pentafluoropropene.*

*43. The method of claim 41, wherein the blend has a boiling point of about −20° C.±0.5° C. at a pressure of about 14.3 psia±2 psia.*

*44. The method of claim 41, wherein the blend has a boiling point of about −20° C. at a pressure of about 14.3 psia.*

*45. The method of claim 41, wherein the blend has a boiling point of about −20.3° C. at a pressure of about 14.39 psia.*

*46. A method, comprising:*

*removing 1,2,3,3,3-pentafluoropropene from a mixture containing 1,2,3,3,3-pentafluoropropene and at least one impurity, comprising:*

*adding water to the mixture in an effective amount to form an azeotropic or azeotrope-like composition of the 1,2,3,3,3-pentafluoropropene and the water;*

*wherein water is provided in an amount from about 0.25 to about 11 weight percent and 1,2,3,3,3-pentafluoropropene is provided in an amount from about 89 to about 99.75 weight percent; and*

*separating the azeotropic composition from the impurity; and*

*producing 2,3,3,3-tetrafluoro-1-propene from the 1,2,3,3,3-pentafluoropropene.*

*47. The method of claim 46, wherein the azeotropic or azeotrope-like composition consists of water and 1,2,3,3,3-pentafluoropropene.*

*48. The method of claim 46, wherein the azeotropic or azeotrope-like composition has a boiling point of about −20° C.±0.5° C. at a pressure of about 14.3 psia±2 psia.*

*49. The method of claim 46, wherein the azeotropic or azeotrope-like composition has a boiling point of about −20° C. at a pressure of about 14.3 psia.*

*50. The method of claim 46, wherein the azeotropic or azeotrope-like composition has a boiling point of about −20.3° C. at a pressure of about 14.39 psia.*

*51. The method of claim 46, wherein the impurity is selected from the group consisting of hydrogen fluoride; 1,1,1,2,3,3-hexafluoropropane (HFC-236ea); 1,1,1,2,3-pentafluoropropane (HFC-245eb); hexafluoropropylene (HFP); 1,1,1,2-tetrafluoropropene (HFO-1234yf); and combinations thereof.*

*52. The method of claim 46,*

*wherein the impurity comprises hydrogen fluoride.*

*53. The method of claim 46,*

*wherein the impurity comprises 1,1,1,2,3,3-hexafluoropropane (HFC-236ea).*

*54. The method of claim 46,*

*wherein the impurity comprises 1,1,1,2,3-pentafluoropropane (HFC-245eb).*

*55. The method of claim 46,*

*wherein the impurity comprises hexafluoropropylene (HFP).*

*56. The method of claim 46,*

*wherein the impurity comprises 1,1,1,2-tetrafluoropropene (HFO-1234yf).*

*57. A method, comprising:*

*providing an azeotropic mixture containing 1,2,3,3,3-pentafluoropropene and water;*

*separating 1,2,3,3,3-pentafluoropropene from the water in the azeotropic mixture;*

*wherein water is provided in an amount from about 0.25 to about 11 weight percent and 1,2,3,3,3-pentafluoropropene is provided in an amount from about 89 to about 99.75 weight percent; and*

*producing 2,3,3,3-tetrafluoro-1-propene from the 1,2,3,3,3-pentafluoropropene.*

*58. The method of claim 57, wherein the azeotropic mixture consists of water and 1,2,3,3,3-pentafluoropropene.*

*59. The method of claim 57, wherein the azeotropic mixture has a boiling point of about −20° C.±0.5° C. at a pressure of about 14.3 psia±2 psia.*

*60. The method of claim 57, wherein the azeotropic mixture has a boiling point of about −20° C. at a pressure of about 14.3 psia.*

*61. The method of claim 57, wherein the azeotropic mixture has a boiling point of about −20.3° C. at a pressure of about 14.39 psia.*

*62. The method of claim 57, wherein 1,2,3,3,3-pentafluoropropene is separated from water using a liquid-liquid phase separation.*

*63. The method of claim 57, wherein 1,2,3,3,3-pentafluoropropene is separated from water using distillation.*

*64. The method of claim 57, wherein 1,2,3,3,3-pentafluoropropene is separated from water using at least one drying media.*

*65. The method of claim 64, wherein the drying media is selected from the group consisting of a molecular sieve, silica alumina, and combinations thereof.*

*66. The method of claim 57, wherein water is removed first by liquid-liquid phase separation, then by a second method selected from the group consisting of distillation, one or more drying media, and combinations thereof.*

*67. A method, comprising:*

*hydrogenating hexafluoropropylene to produce 1,1,1,2,3,3-hexafluoropropane;*

*dehydrofluorinating the 1,1,1,2,3,3-hexafluoropropane to produce an azeotropic mixture of 1,2,3,3,3-pentafluoropropene and water;*

*wherein water is provided in an amount from about 0.25 to about 11 weight percent and 1,2,3,3,3-pentafluoropropene is provided in an amount from about 89 to about 99.75 weight percent;*

*separating 1,2,3,3,3-pentafluoropropene from the water in the azeotropic mixture; and*

*producing 2,3,3,3-tetrafluoro-1-propene from the 1,2,3,3,3-pentafluoropropene.*

*68. The method of claim 67, wherein the azeotropic mixture consists of water and 1,2,3,3,3-pentafluoropropene.*

*69. The method of claim 67, wherein the azeotropic mixture has a boiling point of about −20° C.±0.5° C. at a pressure of about 14.3 psia±2 psia.*

*70. The method of claim 67, wherein the azeotropic mixture has a boiling point of about −20° C. at a pressure of about 14.3 psia.*

*71. The method of claim 67, wherein the azeotropic mixture has a boiling point of about −20.3° C. at a pressure of about 14.39 psia.*

*72. A method, comprising:*

*hydrogenating hexafluoropropylene to produce 1,1,1,2,3,3-hexafluoropropane;*

*dehydrofluorinating the 1,1,1,2,3,3-hexafluoropropane to produce 1,2,3,3,3-pentafluoropropene and water;*

*providing an azeotropic mixture containing 1,2,3,3,3-pentafluoropropene and water;*

*wherein water is provided in an amount from about 0.25 to about 11 weight percent and 1,2,3,3,3-pentafluoropropene is provided in an amount from about 89 to about 99.75 weight percent; separating 1,2,3,3,3-pentafluoropropene from the water in the azeotropic mixture; and*

*producing 2,3,3,3-tetrafluoro-1-propene from the 1,2,3,3,3-pentafluoropropene.*

*73. The method of claim 72, wherein the azeotropic mixture consists of water and 1,2,3,3,3-pentafluoropropene.*

*74. The method of claim 72, wherein the azeotropic mixture has a boiling point of about −20° C.±0.5° C. at a pressure of about 14.3 psia±2 psia.*

*75. The method of claim 72, wherein the azeotropic mixture has a boiling point of about −20° C. at a pressure of about 14.3 psia.*

*76. The method of claim 72, wherein the azeotropic mixture has a boiling point of about −20.3° C. at a pressure of about 14.39 psia.*

*77. A method, comprising:*

*hydrogenating hexafluoropropylene to produce 1,1,1,2,3,3-hexafluoropropane;*

*dehydrofluorinating the 1,1,1,2,3,3-hexafluoropropane to produce 1,2,3,3,3-pentafluoropropene and water;*

*removing an azeotropic mixture of 1,2,3,3,3-pentafluoropropene and water;*

*wherein water is provided in an amount from about 0.25 to about 11 weight percent and 1,2,3,3,3-pentafluoropropene is provided in an amount from about 89 to about 99.75 weight percent*

*separating the 1,2,3,3,3-pentafluoropropene from the water in the azeotropic mixture; and*

*producing 2,3,3,3-tetrafluoro-1-propene from the 1,2,3,3,3-pentafluoropropene.*

*78. The method of claim 77, wherein the azeotropic mixture consists of water and 1,2,3,3,3-pentafluoropropene.*

*79. The method of claim 77, wherein the azeotropic mixture has a boiling point of about −20° C.±0.5° C. at a pressure of about 14.3 psia±2 psia.*

*80. The method of claim 77, wherein the azeotropic mixture has a boiling point of about −20° C. at a pressure of about 14.3 psia.*

*81. The method of claim 77, wherein the azeotropic mixture has a boiling point of about −20.3° C. at a pressure of about 14.39 psia.*

*82. A method, comprising:*

*dehydrofluorinating 1,1,1,2,3,3-hexafluoropropane to produce 1,2,3,3,3-pentafluoropropene and water;*

*removing an azeotropic mixture of 1,2,3,3,3-pentafluoropropene and water;*

*wherein water is provided in an amount from about 0.25 to about 11 weight percent and 1,2,3,3,3-pentafluoropropene is provided in an amount from about 89 to about 99.75 weight percent;*

*separating the 1,2,3,3,3-pentafluoropropene from the water in the azeotropic mixture; and*

*producing 2,3,3,3-tetrafluoro-1-propene from the 1,2,3,3,3-pentafluoropropene.*

*83. The method of claim 82, wherein the azeotropic mixture consists of water and 1,2,3,3,3-pentafluoropropene.*

*84. The method of claim 82, wherein the azeotropic mixture has a boiling point of about −20° C.±0.5° C. at a pressure of about 14.3 psia±2 psia.*

*85. The method of claim 82, wherein the azeotropic mixture has a boiling point of about −20° C. at a pressure of about 14.3 psia.*

*86. The method of claim 82, wherein the azeotropic mixture has a boiling point of about −20.3° C. at a pressure of about 14.39 psia.*

*87. A method, comprising:*

*forming an azeotropic composition consisting essentially of effective amounts of water and 1,2,3,3,3-pentafluoropropene;*

*producing 2,3,3,3-tetrafluoro-1-propene from the 1,2,3,3,3-pentafluoropropene.*

*88. A method of claim 87, wherein water is provided in an amount from about 0.25 to about 11 weight percent and 1,2,3,3,3-pentafluoropropene is provided in an amount from about 89 to about 99.75 weight percent.*

*89. A method, comprising:*

*hydrogenating hexafluoropropylene to produce 1,1,1,2,3,3-hexafluoropropane;*

*dehydrofluorinating the 1,1,1,2,3,3-hexafluoropropane to produce 1,2,3,3,3-pentafluoropropene and water;*

*providing an azeotropic mixture containing 1,2,3,3,3-pentafluoropropene and water; and*

*producing 2,3,3,3-tetrafluoro-1-propene from the 1,2,3,3,3-pentafluoropropene.*

*90. A method of claim 89, wherein water is provided in an amount from about 0.25 to about 11 weight percent and 1,2,3,3,3-pentafluoropropene is provided in an amount from about 89 to about 99.75 weight percent in the azeotropic mixture.*

*91. The method of claim 89, wherein the azeotropic mixture consists of water and 1,2,3,3,3-pentafluoropropene.*

*92. The method of claim 89, wherein the azeotropic mixture has a boiling point of about −20° C.±0.5° C. at a pressure of about 14.3 psia±2 psia.*

*93. The method of claim 89, wherein the azeotropic mixture has a boiling point of about −20° C. at a pressure of about 14.3 psia.*

*94. The method of claim 89, wherein the azeotropic mixture has a boiling point of about −20.3° C. at a pressure of about 14.39 psia.*

*95. A method, comprising:*

*hydrogenating hexafluoropropylene to produce 1,1,1,2,3,3-hexafluoropropane;*

*dehydrofluorinating the 1,1,1,2,3,3-hexafluoropropane to produce 1,2,3,3,3-pentafluoropropene and water;*

*removing an azeotropic mixture of 1,2,3,3,3-pentafluoropropene and water;*

*separating the 1,2,3,3,3-pentafluoropropene from the water in the azeotropic mixture; and*

*producing 2,3,3,3-tetrafluoro-1-propene from the 1,2,3,3,3-pentafluoropropene.*

*96. A method of claim 95, wherein water is provided in an amount from about 0.25 to about 11 weight percent and 1,2,3,3,3-pentafluoropropene is provided in an amount from about 89 to about 99.75 weight percent in the azeotropic mixture.*

*97. The method of claim 95, wherein the azeotropic mixture consists of water and 1,2,3,3,3-pentafluoropropene.*

*98. The method of claim 95, wherein the azeotropic mixture has a boiling point of about −20° C.±0.5° C. at a pressure of about 14.3 psia±2 psia.*

*99. The method of claim 95, wherein the azeotropic mixture has a boiling point of about −20° C. at a pressure of about 14.3 psia.*

*100. The method of claim 95, wherein the azeotropic mixture has a boiling point of about −20.3° C. at a pressure of about 14.39 psia.*

*101. A method, comprising:*

*dehydrofluorinating 1,1,1,2,3,3-hexafluoropropane to produce 1,2,3,3,3-pentafluoropropene and water;*

*removing an azeotropic mixture of 1,2,3,3,3-pentafluoropropene and water;*

*separating the 1,2,3,3,3-pentafluoropropene from the water in the azeotropic mixture; and*

*producing 2,3,3,3-tetrafluoro-1-propene from the 1,2,3,3,3-pentafluoropropene.*

*102. A method of claim 101, wherein water is provided in an amount from about 0.25 to about 11 weight percent and 1,2,3,3,3-pentafluoropropene is provided in an amount from about 89 to about 99.75 weight percent.*

*103. The method of claim 101, wherein the azeotropic mixture consists of water and 1,2,3,3,3-pentafluoropropene.*

*104. The method of claim 101, wherein the azeotropic mixture has a boiling point of about −20° C.±0.5° C. at a pressure of about 14.3 psia±2 psia.*

*105. The method of claim 101, wherein the azeotropic mixture has a boiling point of about −20° C. at a pressure of about 14.3 psia.*

*106. The method of claim 101, wherein the azeotropic mixture has a boiling point of about −20.3° C. at a pressure of about 14.39 psia.*

*107. A method, comprising:*

*dehydrofluorinating 1,1,1,2,3,3-hexafluoropropane to produce 1,2,3,3,3-pentafluoropropene and water;*

*removing an azeotropic mixture of 1,2,3,3,3-pentafluoropropene and water;*

*separating the 1,2,3,3,3-pentafluoropropene from the water in the azeotropic mixture; and*

*producing a hydrofluoroolefin from the 1,2,3,3,3-pentafluoropropene.*

*108. The method of claim 107,*

*wherein the hydrofluoroolefin is 2,3,3,3-tetrafluoro-1-propene.*

* * * * *